(12) United States Patent
Rivier et al.

(10) Patent No.: US 12,131,210 B2
(45) Date of Patent: Oct. 29, 2024

(54) MEDICAL CONTAINER COMPRISING A RFID TAG FOR REMOTE IDENTIFICATION OF SAID MEDICAL CONTAINER

(71) Applicants: Becton Dickinson France, Le Pont-de-Claix (FR); Becton, Dickinson and Company, Franklin Lakes, NJ (US)

(72) Inventors: Cédric Rivier, Voreppe (FR); Nicolas Euvrard, London (GB)

(73) Assignees: Becton Dickinson France, Le Pont-de-Claix (FR); Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 18/027,000

(22) PCT Filed: Sep. 15, 2021

(86) PCT No.: PCT/EP2021/075395
§ 371 (c)(1),
(2) Date: Mar. 17, 2023

(87) PCT Pub. No.: WO2022/058394
PCT Pub. Date: Mar. 24, 2022

(65) Prior Publication Data
US 2023/0367987 A1  Nov. 16, 2023

(30) Foreign Application Priority Data

Sep. 18, 2020 (EP) ..................................... 20306050

(51) Int. Cl.
*G06K 19/077* (2006.01)

(52) U.S. Cl.
CPC . *G06K 19/07758* (2013.01); *G06K 19/07773* (2013.01)

(58) Field of Classification Search
CPC ................... G06K 19/07758; G06K 19/07773
USPC ......................................................... 235/492
See application file for complete search history.

(56) References Cited

U.S. PATENT DOCUMENTS

| | | | |
|---|---|---|---|
| 9,305,283 B1 * | 4/2016 | Lauka ................. | G06K 7/10237 |
| 11,752,274 B2 * | 9/2023 | Nisha ................. | A61M 5/31568 |
| | | | 604/218 |
| 2006/0186204 A1 | 8/2006 | Lubow | |
| 2006/0232413 A1 | 10/2006 | Lam et al. | |
| 2013/0194148 A1 * | 8/2013 | Fontecchio .......... | H01Q 1/2208 |
| | | | 427/560 |
| 2014/0184390 A1 * | 7/2014 | Elizondo, II ..... | G06K 19/07786 |
| | | | 340/10.1 |
| 2015/0186768 A1 * | 7/2015 | Peters .............. | G06K 19/07743 |
| | | | 235/492 |

(Continued)

FOREIGN PATENT DOCUMENTS

| WO | 2017157784 A1 | 9/2017 |
|---|---|---|
| WO | 2019189451 A1 | 10/2019 |

*Primary Examiner* — Allyson N Trail
(74) *Attorney, Agent, or Firm* — The Webb Law Firm

(57) ABSTRACT

A medical container including a tubular barrel defining a reservoir for a medical product. The barrel is provided with a scale having graduations indicative of an injected volume or a remaining volume of said medical product. The barrel further includes a RFID tag including an antenna that forms, follows or overlays with at least a portion of the scale.

16 Claims, 2 Drawing Sheets

(56) References Cited

U.S. PATENT DOCUMENTS

| | | | |
|---|---|---|---|
| 2016/0254586 A1* | 9/2016 | Shimo | B60J 3/007 |
| | | | 343/713 |
| 2016/0296692 A1* | 10/2016 | Agris, III | A61M 5/007 |
| 2017/0124264 A1 | 5/2017 | Jordan et al. | |
| 2018/0093042 A1 | 4/2018 | Klemm et al. | |
| 2020/0202192 A1* | 6/2020 | Hu | G06K 19/06028 |
| 2020/0265289 A1* | 8/2020 | Kapp | G06K 19/07709 |
| 2021/0008275 A1* | 1/2021 | Okuda | A61M 5/3135 |
| 2021/0008295 A1 | 1/2021 | Okuda | |
| 2023/0004771 A1* | 1/2023 | Kuechenthal | G06K 19/0723 |
| 2023/0395966 A1* | 12/2023 | Shimada | G06K 19/07756 |

* cited by examiner

MEDICAL CONTAINER COMPRISING A RFID TAG FOR REMOTE IDENTIFICATION OF SAID MEDICAL CONTAINER

CROSS-REFERENCE TO RELATED APPLICATIONS

This application is the United States national phase of International Application No. PCT/EP2021/075395 filed Sep. 15, 2021, and claims priority to European Patent Application No. 20306050.4 filed Sep. 18, 2020, the disclosures of which are hereby incorporated by reference in their entireties.

BACKGROUND OF THE INVENTION

Field of the Invention

The present invention relates to a medical container comprising a RFID tag and a method for manufacturing said medical container.

Description of Related Art

In this application, the distal end of a component or of a device is to be understood as meaning the end furthest from the user's hand and the proximal end is to be understood as meaning the end closest to the user's hand. Likewise, in this application, the "distal direction" is to be understood as meaning the direction of injection, with respect to a medical container of the invention, and the "proximal direction" is to be understood as meaning the opposite direction to said direction of injection, that is to say the direction towards the user's hand holding a container as for an injection operation.

Medical injection devices, for example pre-fillable or prefilled syringes, usually comprise a hollow body or barrel forming a container for a medical product. This body comprises a distal end, optionally provided with a needle, and a proximal end, usually provided with a flange.

There is an increasing need for individual traceability of the medical containers, such as medical injection devices, from the manufacturing process until the final labeling, the final use or the disposal of said medical containers.

It is known, for example, from WO2017157784, a receptacle having a cylindrical lateral surface surrounded by a sequence of printed machine-readable unique identifier codes. These printed unique identifier codes allow tracking of each receptacle along a supply chain. However, these unique identifier codes are printed on an external side of the receptacle so that they may be removed or damaged, for example, during handling or use of the receptacle. Moreover, the unique identifier codes cover a portion of the receptacle so that they may have an impact on a user visual inspection process. Finally, an inkjet printer is used to print the identifier codes on the external side of the receptacle. However, this printing method, using ink, may lead to a risk of contamination of the receptacle. Moreover, one may not have access to these printed unique identifier codes when the receptacle is put, for example, in a sealed packaging.

It is known from the document WO 2019189451 a pre-filled syringe comprising a RFID tag positioned on the insertion section of the syringe plunger. The document US20060186204 discloses a combined multi-frequency electromagnetic and optical communication system. The document US20060232413 discloses a RFID tag with an antenna comprising an optical code. The document US20180093042 discloses a sensor for capacitive determination of a filling level.

SUMMARY OF THE INVENTION

In this context, an object of the present invention is to provide a device that alleviates the above-mentioned drawbacks by allowing an efficient individual identification of a medical container with a limited impact on visual inspection, with a limited impact on the manufacturing process and with an improved reading range.

A first aspect of the invention is a medical container comprising a tubular barrel defining a reservoir for a medical product, the barrel being provided with a scale having graduations indicative of an injected volume or a remaining volume of said medical product, the barrel further comprising a RFID tag, the medical container being characterized in that the RFID tag comprises an antenna that forms, follows or overlays with at least a portion of the scale.

The medical container of the invention therefore allows individual traceability of each medical container from the manufacturing process to the final use of the medical container. Indeed, the RFID tag comprised in the medical container of the invention allows remote identification of said medical container. The fact that the antenna forms, follows or overlays with at least a portion of the scale permits to increase the antenna length, thereby improving the reading range. Besides, there is a limited impact on product aspect, hence on visual inspection because the antenna is close to the scale, or even forms or overlays with the scale. There is also a limited impact on the product image at the end user.

By antenna forming at least a portion of the scale it should be understood that the antenna itself may be said at least one portion of the scale. Without the antenna, there is thus no such portion of the scale. It should be noted that the antenna may form the complete scale.

Alternatively, by antenna following at least a portion of the scale it is should be understood that the antenna may extend contiguous to said at least one portion of the scale. As a result, the antenna may run alongside the scale, and/or may intersect the scale, for instance at one or several graduation marks if any.

By antenna overlaying with the at least one portion of the scale it should be understood that the antenna is superjacent to said at least one portion of the scale and thus extends on the outline of the scale.

In an embodiment, the RFID tag includes a chip, the chip and the antenna being applied on a transparent substrate.

The substrate allows maintaining the chip and the antenna together, and the substrate's transparency aims at further limiting the impact on the medical container visual inspection.

In an embodiment, the substrate is provided with an adhesive for attachment of the RFID tag to the barrel.

This permits a limited impact on the manufacturing process.

In an embodiment, the chip and/or the antenna of the RFID tag are formed by ceramic metallic printing, metallic printing or graphene printing, etching or stamping.

In an advantageous embodiment, at least the antenna of the RFID tag is formed by graphene, metallic or ceramic metallic printing directly onto an external wall of the barrel. The chip of the RFID tag may also be formed by metallic printing or graphene printing.

This enables very thin chip and antenna, hence having an even more limited impact on the medical container external dimensions.

Preferably, the RFID tag is an Ultra-High Frequency RFID tag (UHF-RFID).

Preferably, the antenna is a dipole antenna comprising two legs attached to a chip of the RFID tag, each of said legs forming, following, or overlaying with the at least one portion of the scale.

Preferably, one of said legs extends proximal to the chip while the other leg extends distal to the chip.

This improves the reading range.

In an embodiment, the RFID tag includes a chip that is no wider than the antenna.

This limits the impact on visual inspection of the medical container. The chip may thus be hidden by the scale that may be formed by the antenna.

In an embodiment, the scale is a graduated scale. Also, the antenna may have anyone of a straight line, or a sine, a square, a triangle, a sawtooth or a pulse waveform.

Therefore, the antenna may form or overlay with any of the graduations of the graduated scale.

Another aspect of the invention is a method for manufacturing the above-described medical container, the method comprising the steps of forming a RFID antenna that forms, follows or overlays with at least a portion of the barrel scale.

In an embodiment, the method comprises the steps of:
(i) applying the antenna and a chip of the RFID tag on a transparent substrate, for example by printing, etching or stamping;
(ii) applying the substrate onto an external wall of the barrel, preferably by means of an adhesive;
(iii) storing a Unique Device Identifier (UDI) into the RFID tag.

In an alternative embodiment, the method comprises the steps of:
(i) applying at least the antenna of the RFID tag directly on an external wall of the barrel, preferably by ceramic metallic, metallic or graphene printing;
(ii) storing a Unique Device Identifier (UDI) into the RFID tag.

BRIEF DESCRIPTION OF THE DRAWINGS

The invention and the advantages arising therefrom will clearly emerge from the detailed description that is given below with reference to the appended drawings as follows.

DESCRIPTION OF THE INVENTION

Figure 1:
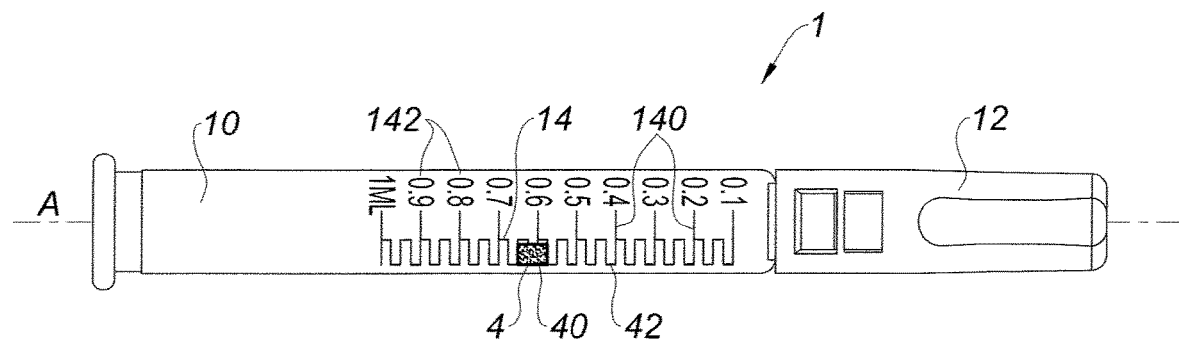
FIG. 1 is a side view of a medical container according an embodiment of the invention.

With reference to FIG. 1 is shown a medical container 1, such as a pre-fillable or prefilled syringe, according to an embodiment of the invention. The medical container could also be a vial, a cartridge, or any medical container on which a volumetric scale may be implemented. The medical container 1 comprises a cylindrical barrel 10 defining a reservoir for containing a medical product. The barrel 10 extends along a longitudinal axis A and has a distal end (not shown) that may be in the form of a longitudinal distal tip defining a fluid passageway in fluid communication with the reservoir. As shown on FIG. 1, a cap 12 may cover the distal tip before use of the medical container 1. The medical container 1 may also include a plunger rod (not shown) having a plunger stopper at a distal end thereof so as to expel the medical product contained in the reservoir. The barrel 10 may be made of a glass or a plastic material.

Figure 2:
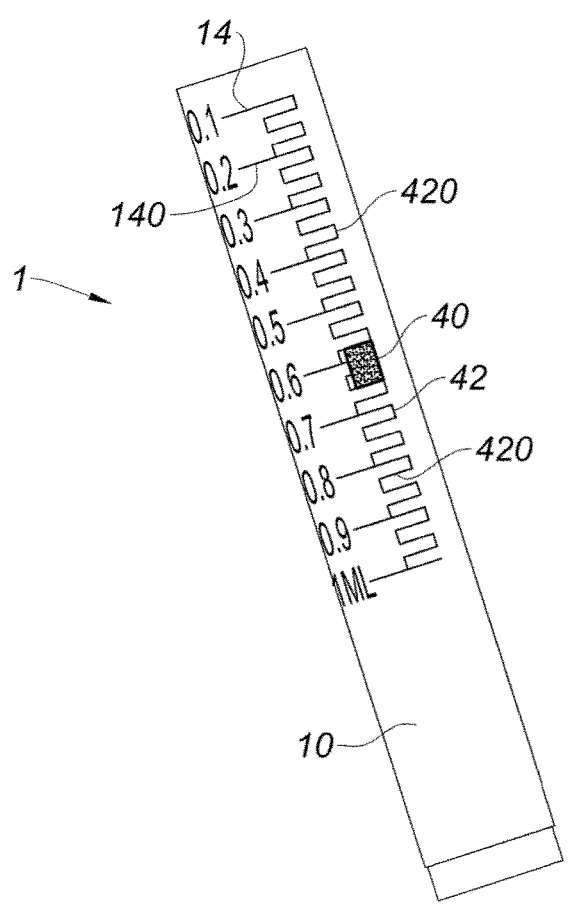
FIG. 2 is a perspective view of the barrel of a medical container according to an embodiment of the invention.

As visible on FIG. 1 or 2, the barrel 10 has a graduated scale 14 extending parallel to the longitudinal axis A. The graduated scale 14 includes graduation marks 140. The graduation marks 140 may be indicative of a remaining volume of the medical product inside the reservoir or of the already injected medical product during use of the medical container 1. The graduation marks 140 may be orthogonal to the longitudinal axis A and may also be parallel to each other. A FIG. 142 indicative of a volume amount may be located adjacent to specific graduation line 140.

Still with reference to FIGS. 1 and 2, the medical container 1 further comprises a RFID tag 4, preferably a passive tag, located on the barrel 10. The RFID tag 4 is configured to allow remote identification of the medical container 1. The RFID tag 4 includes a chip 40 and an antenna 42. The chip 40 may include a memory for storing a Unique Device Identifier (UDI), and additional data such as product code or batch number.

According to the invention, the antenna 42 partially or completely forms, follows, or overlays with the graduated scale 14. In the example shown on FIGS. 1 and 2, the antenna 42 completely forms the graduated scale 14. That is, the antenna 42 is the graduated scale 14. In other embodiments not shown, the antenna 42 may be added to the barrel 10 such that the antenna 42 is contiguous to, or overlays with an already existing graduated scale 14. The fact that the antenna 42 itself forms, or extends along, or is superjacent with the graduated scale 14 or at least a portion of the graduated scale 14 enables to limit the visual impact on the medical container 1 appearance.

In an embodiment not shown, the medical container 1 may for instance include already existing graduation marks 140 and the antenna 42 may extend parallel to the longitudinal axis A so as to connect said graduation marks 140. In another embodiment (not shown), the antenna 42 may only form one or several graduation marks 140.

In the example of FIGS. 1 and 2, the antenna 42 substantially extends parallel to a longitudinal axis A of the medical container 1, and defines peaks orthogonal to said longitudinal axis A at predetermined intervals along the barrel 10. These peaks form the graduation marks 140.

Figure 4:
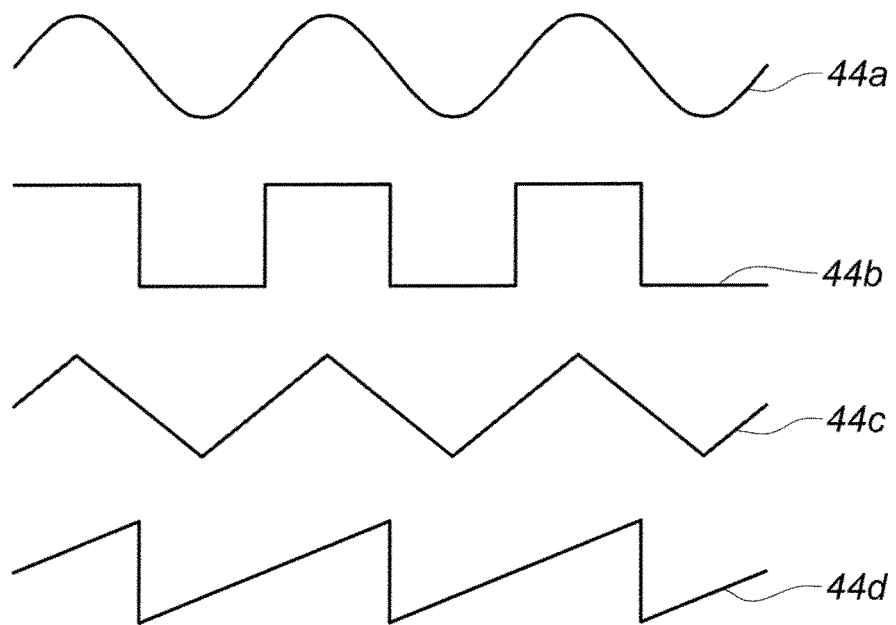
FIG. 4 is a view illustrating different possible shapes of the antenna of the RFID tag of the medical container according to an embodiment of the invention.

Although the antenna 42 shown on FIGS. 1 and 2 has a square waveform forming the graduated scale 14, it is contemplated that any other form defining graduation marks 140 along the longitudinal axis A of the barrel 10 might be appropriate. For example, as illustrated on FIG. 4, the antenna 42 may have anyone of a sine 44a, a square 44b, a triangle 44c, a sawtooth 44d or a pulse waveform. Alternatively, the antenna 42 may also be shaped as a straight line extending along the longitudinal axis A, the graduation marks 140 not being overlaid or superjacent with the antenna 42. Otherwise, the graduated scale 14 may have a substantially ring shape designed around an outer wall of the barrel 10. Accordingly, the antenna 42 may follow the shape of such ring-shaped graduated scale 14.

Figure 3:
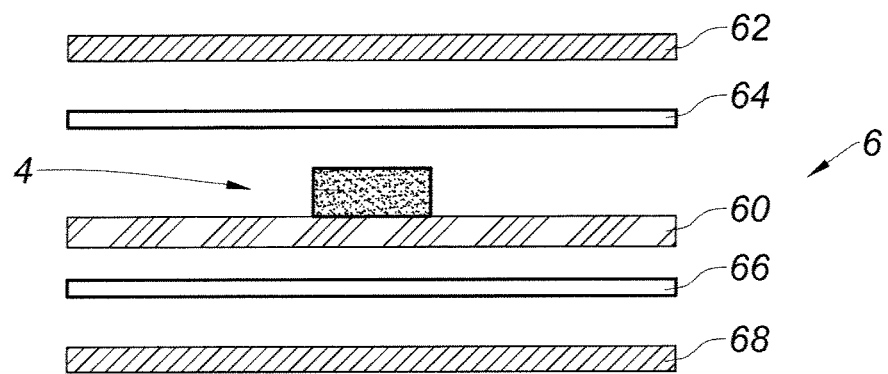
FIG. 3 is a schematic view of a RFID tag of a medical container according to an embodiment of the invention.

With reference to FIG. 3, the RFID tag 4 may be in a form of a transparent wet inlay 6. Alternatively, the RFID tag 4 may be in a form of a dry inlay or a pressure sensitive label. RFID Wet Inlays 6 and RFID Dry Inlays can comprise a substrate 60, for example made of paper or Polyethylene terephthalate (PET). The RFID tag 4 can be disposed on one side of the substrate 60. RFID Wet Inlays and RFID Dry Inlays can further comprise at least one protective layer 62, such as a siliconized paper, on top of the RFID tag 4. The protective layer 62 may be attached by means of an adhesive layer 64.

RFID Wet Inlays are described as "wet" as they include an adhesive backing 66 on the other side of the substrate 60 and a backing paper 68, for example a silicon liner. RFID Wet Inlays are like RFID stickers and are ideal for applications which require a "peel and stick" type of tag. RFID Dry Inlays are described as "dry" due to their lack of adhesive backing. Pressure-sensitive labels are analogous to a high-tech sticker.

It should be noted that the RFID inlay 6 is configured to resist to sterilization processes such as steam sterilization, e-beam sterilization, vapor hydrogen peroxide sterilization, or EtO sterilization.

In one embodiment, the chip 40 and/or the antenna 42 may be formed by ceramic metallic printing, metallic printing or graphene printing. They may also be formed by etching or stamping, except when they are directly formed onto the barrel 10. The ceramic metallic, metallic or graphene printing may be made on the RFID inlay 6, or directly on the external wall of the barrel 10. When the chip 40 and/or the antenna 42 are directly printed on the external wall of the barrel 10, there may be no need for a RFID inlay 6 and more specifically no need for a substrate other than the barrel itself nor for an adhesive. Preferably, at least the antenna 42 is formed by metallic printing, ceramic metallic printing or graphene printing.

The RFID tag 4 may be a Low Frequency (about 30 KHz to 300 KHz) RFID tag 4 (LF-RFID), a High Frequency (about 1-15 MHz) RFID tag 4 (HF-RFID) or, preferably, an Ultra-High Frequency (about 400-1000 MHz) RFID tag 4 (UHF-RFID). A RFID reader can for example read the LF-RFID tag 4 at a distance up to about 10 cm, the HF-RFID tag 4 at a distance of about one meter and the UHF-RFID tag 4 at a distance of about fifteen meters.

The RFID tag 4 may also be a High-Frequency Near Field Communication (HF-NFC) tag. The frequencies are usually about 13.56 MHz. In this embodiment, a NFC reader can for example read the HF-NFC tag at a distance up to a few centimeters. HF-NFC differs from HF-RFID in that it can be read by a NFC smartphone. In one embodiment, the RFID tag 4 is a double frequency tag including simultaneously a HF-NFC and an UHF RFID. For example, it can be read with both a NFC smartphone or an UHF reader.

With reference to FIG. 2 where the RFID tag 4 is a UHF-RFID tag 4, the antenna 42 may be a dipole-shaped antenna 42 comprising two legs 420 attached to the chip 40. Each of said legs 420 forms, follows, or overlays with at least a portion of the graduated scale 14 or the complete graduated scale 14. Preferably, one of said legs 420 extends proximal to the chip 40 while the other leg 420 extends distal to the chip 40.

Depending on the frequencies used (UHF, HF, LF, NFC) different designs of antenna 42 are possible. For instance, when the RFID tag 4 is a HF-RFID or NFC-RFID, the antenna 42 may have a substantially ring shape and may thus form one graduation line of the graduated scale 14.

In an embodiment, the RFID tag 4 includes a chip 40 that is no wider than the antenna 42 so that the chip 40 can be hidden within the scale pattern thanks to its small size. For example the chip 40 may be about 1 mm-wide. The antenna 42 and the chip 40, usually the thickest element of the RFID tag 4, are thin enough so that they add limited extra layer to the RFID inlay, for a maximum RFID inlay thickness up to 0.5 mm, preferably below 0.4 mm, and ideally below 0.3 mm.

The invention also relates to a method for manufacturing the above-described medical container 1, the method comprising the steps of forming a RFID antenna 42 that forms, follows or overlays with at least a portion of the barrel 10 graduated scale 14.

In an embodiment, the method comprises the step of applying the antenna 42 and a chip 40 of the RFID tag 4 on a transparent substrate 60, for example by printing, etching or stamping. During this first step, the antenna 42 may be first applied onto the substrate 60 for example by printing, etching or stamping, and then the chip 40 may be added onto the substrate 60 which holds the antenna 42 and is bonded to said antenna 42. Further, the method comprises the steps of applying the substrate 60 comprising said RFID tag 4 onto an external wall of the barrel 10, preferably by means of an adhesive, and storing a Unique Device Identifier (UDI) into the RFID tag 4.

In an alternate embodiment, the method comprises the steps of applying the antenna 42 and a chip 40 of the RFID tag 4 on an external wall of the barrel 10, preferably by metallic or graphene printing, and storing a Unique Device Identifier (UDI) into the RFID tag 4.

The invention claimed is:

1. A medical container comprising a tubular barrel defining a reservoir for a medical product, the barrel being provided with a scale having graduations indicative of an injected volume or a remaining volume of said medical product, wherein the barrel further comprises a RFID tag, the RFID tag comprising a visible antenna, the antenna forming and/or overlaying at least a portion of the scale, such that the antenna represents at least a portion of the scale.

2. The medical container according to claim 1, wherein the RFID tag includes a chip, the chip and the antenna being applied on a transparent substrate.

3. The medical container according to claim 2, wherein the substrate is provided with an adhesive for attachment of the RFID tag to the barrel.

4. The medical container according to claim 2, wherein the chip and/or the antenna of the RFID tag are formed by ceramic metallic printing, metallic printing or graphene printing, etching or stamping.

5. The medical container according to claim 1, wherein at least the antenna of the RFID tag is formed by ceramic metallic printing, metallic printing or graphene printing directly onto an external wall of the barrel.

6. The medical container according to claim 1, wherein the RFID tag is an Ultra-High Frequency RFID tag.

7. The medical container according to claim 6, wherein the antenna is a dipole antenna comprising two legs attached to a chip of the RFID tag, each of said legs forming or overlaying with the at least one portion of the scale.

8. The medical container according to claim 7, wherein one of said legs extends proximal to the chip while the other leg extends distal to the chip.

9. The medical container according to claim 1, wherein the RFID tag includes a chip that is no wider than the antenna.

10. The medical container according to claim 1, wherein the antenna has any one of a straight line, or a sine, a square, a triangle, a sawtooth or a pulse waveform.

11. A method for manufacturing a medical container according to claim 1, wherein the method comprises the steps of forming a RFID antenna that forms or overlays with at least a portion of the barrel scale.

12. The method according to claim 11, comprising the steps of:
   (i) applying the antenna and a chip of the RFID tag on a transparent substrate;
   (ii) applying the substrate onto an external wall of the barrel;
   (iii) storing a Unique Device Identifier into the RFID tag.

13. The method according to claim 11, comprising the steps of:
   (i) applying at least the antenna of the RFID tag directly on an external wall of the barrel;
   (ii) storing a Unique Device Identifier into the RFID tag.

14. The medical container according to claim 1, wherein the antenna forms or overlays at least a portion of any graduations of the scale.

15. The medical container according to claim 1, wherein the antenna has an increased antenna length that improves reading range of the scale.

16. The medical container according to claim 1, wherein the antenna forms the graduations of the scale.

\* \* \* \* \*